United States Patent
Baiko et al.

(10) Patent No.: US 11,730,908 B2
(45) Date of Patent: Aug. 22, 2023

(54) MAGNETICALLY ASSISTED SEALING ARRANGEMENT FOR A PATIENT INTERFACE DEVICE

(71) Applicant: KONINKLIJKE PHILIPS N.V., Eindhoven (NL)

(72) Inventors: Robert William Baiko, Pittsburgh, PA (US); Richard Thomas Haibach, Verona, PA (US); Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/872,081

(22) Filed: Jul. 25, 2022

(65) Prior Publication Data

US 2023/0016101 A1    Jan. 19, 2023

Related U.S. Application Data

(62) Division of application No. 16/306,702, filed as application No. PCT/EP2017/063412 on Jun. 2, 2017, now Pat. No. 11,420,000.

(Continued)

(51) Int. Cl.
*A61M 16/06* (2006.01)
*A61M 16/08* (2006.01)

(52) U.S. Cl.
CPC .... *A61M 16/0622* (2014.02); *A61M 16/0605* (2014.02); *A61M 16/0616* (2014.02);
(Continued)

(58) Field of Classification Search
CPC ...... A61M 16/0622; A61M 2016/0661; A61M 16/06; A61M 16/0627; A61M 16/065;
(Continued)

(56) References Cited

U.S. PATENT DOCUMENTS

| 5,850,834 A * | 12/1998 | Yoshida | A61F 5/08 128/204.12 |
| 8,430,098 B1 * | 4/2013 | Buddharaju | A61M 16/0683 128/207.18 |
| 8,651,106 B1 * | 2/2014 | Morgan, Jr. | A62B 23/06 128/205.27 |
| 2005/0139215 A1 * | 6/2005 | Riach | A61N 2/06 128/206.11 |

(Continued)

FOREIGN PATENT DOCUMENTS

| WO | 2011030250 A1 | 3/2011 |
| WO | 2014045245 A1 | 3/2014 |

OTHER PUBLICATIONS

International Search Report for PCT/EP2017/063412 filed Jun. 2, 2017.

*Primary Examiner* — Tu A Vo
(74) *Attorney, Agent, or Firm* — Michael W. Haas (57) ABSTRACT

A sealing arrangement for use in a patient interface device. The sealing arrangement includes a nasal pillow having a sealing surface structured to sealingly engage a surface of the patient at or about the airway. A first magnetic material is disposed in or the nasal pillow. A carrier member is positioned across a nose of the patient. Finally, a second magnetic material is positioned in or on carrier member. The first magnetic material and the second magnetic material magnetically interact in a manner that the sealing surface of the flexible member toward the surface of the patient responsive to the flexible member being disposed at or about the airway and the second magnetic material is disposed at a corresponding position to interact with the first magnetic material.

3 Claims, 11 Drawing Sheets

Related U.S. Application Data (60) Provisional application No. 62/350,743, filed on Jun. 16, 2016.

(52) U.S. Cl.
CPC .... *A61M 16/0666* (2013.01); *A61M 16/0683* (2013.01); *A61M 16/0816* (2013.01); *A61M 16/0633* (2014.02); *A61M 2205/0272* (2013.01); *A61M 2209/088* (2013.01)

(58) Field of Classification Search
CPC .......... A61M 16/0655; A61M 16/0644; A61M 16/0638; A61M 16/0605; A61M 16/0616; A61M 16/0666; A61M 16/0683; A61M 16/0816; A61M 16/0633; A61M 2205/0272; A61M 16/0694; A61M 16/0672; A61M 16/0688; A61M 16/0677; A61M 16/0611; A62B 18/00; A62B 18/02; A62B 18/025; A62B 18/04; A62B 18/06; A62B 18/08; A62B 18/084; A62B 23/06

See application file for complete search history.

(56) References Cited

U.S. PATENT DOCUMENTS

| | | | | |
|---|---|---|---|---|
| 2010/0307497 | A1 | 12/2010 | Busch | |
| 2011/0067704 | A1* | 3/2011 | Kooij | A61M 16/0858 128/207.18 |
| 2011/0220112 | A1 | 9/2011 | Connor | |
| 2011/0315141 | A1* | 12/2011 | Lavi | A61M 16/0816 128/204.23 |
| 2012/0167892 | A1* | 7/2012 | Matula, Jr. | A61M 16/085 128/206.21 |
| 2013/0112206 | A1* | 5/2013 | Buddharaju | A61M 16/0057 128/206.25 |
| 2014/0251340 | A1* | 9/2014 | Pastoor | A61M 16/0683 128/207.18 |
| 2014/0360503 | A1 | 12/2014 | Franklin | |
| 2015/0034098 | A1* | 2/2015 | Schumacher | A41D 13/1138 128/863 |
| 2015/0250972 | A1 | 9/2015 | Haibach | |
| 2015/0283349 | A1 | 10/2015 | Mclaren | |
| 2015/0314113 | A1* | 11/2015 | Castillo | A61F 5/08 606/199 |
| 2015/0335846 | A1 | 11/2015 | Romagnoli | |

\* cited by examiner

MAGNETICALLY ASSISTED SEALING ARRANGEMENT FOR A PATIENT INTERFACE DEVICE

CROSS-REFERENCE TO PRIOR APPLICATIONS

This application is a divisional application and claims the priority benefit of U.S. application Ser. No. 16/306,702, filed Dec. 3, 2018, which claims the priority benefit under 35 U.S.C. § 371 of International Patent Application No. PCT/EP2017/063412, filed on Jun. 2, 2017, which claims the priority benefit under 35 U.S.C. § 119(e) of U.S. Patent Application No. 62/350,743, filed on Jun. 16, 2016, the contents of which are herein incorporated by reference.

BACKGROUND OF THE INVENTION

1. Field of the Invention

The present invention pertains to a magnetically assisted sealing arrangement for a patient interface for delivering a flow of breathing gas to the airway of a patient. The present invention also pertains to a cushion member for use in a patient interface device, the cushion member having a sealing arrangement that is magnetically assisted. The present invention further pertains to an interface device for use in delivering a flow of breathing gas to the airway of a particular patient having a magnetically assisted sealing arrangement.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such masks are typically worn for an extended period of time, a variety of concerns must be taken into consideration. For example, in providing CPAP to treat obstructive sleep apnea (OSA), the patient normally wears the patient interface device all night long while he or she sleeps. One concern in such a situation is that an optimum seal is created between the patient interface device and the patient, as any leakage can be both undesirable to the patient and can necessitate the use of higher treatment pressures. Another concern is that the patient interface device is as comfortable as possible; otherwise the patient may avoid wearing the interface device, defeating the purpose of the prescribed pressure support therapy.

A common problem with current CPAP patient interface devices is the mismatch of geometry that occurs between the mask and patient's face. Such mismatch can result in leaks and patient discomfort. Therapy pressure can be used to partially assist in getting the ceiling flap of the mask to conform to the facial geometry of the patient but at times internal flap forces prevent a full robust seal. Providing outside force to assist the therapy pressure and locating and providing more force on the mask can help to get the mask to fully seal against the patient's face. Such outside force is commonly applied via straps. However, the application of such outside forces can cause the mask to be generally uncomfortable to wear, thus leading to the patient to tend to not adhere to the proscribed therapy.

SUMMARY OF THE INVENTION

Accordingly, it is an object of the present invention to provide a sealing arrangement for use in a patient interface device for delivering a flow of breathing gas to an airway of a patient. The sealing arrangement comprises a flexible member formed substantially from a first material, the flexible member having a sealing surface structured to sealingly engage a surface of the patient at or about the airway, the flexible member including a first magnetic material disposed in or on the first material. The sealing arrangement further comprises a second magnetic material positioned in or on one or more of: a carrier member structured to be removably positioned on, in, or about the patient, and a portion of the patient interface device. The first magnetic material and the second magnetic material are positioned and structured to magnetically interact in a manner which urges the sealing surface of the flexible member toward the surface of the patient when the flexible member is disposed at or about the airway and the second magnetic material is disposed at a corresponding position to interact with the first magnetic material.

The first magnetic material may comprise a plurality of magnetic particles dispersed within, or provided on, the flexible member. The first magnetic material may comprise at least one discrete magnet disposed within, or provided on, the flexible member.

The flexible member may comprise a sealing flap of a cushion, the cushion may comprise a support portion underlying the sealing flap, and the second magnetic material may be disposed in or on the support portion such that the flexible member is urged in a direction away from the support portion by the magnetic interaction between the second magnetic material and the first magnetic material.

The second magnetic material may be disposed in the carrier member and the carrier member may be structured to be removeably disposed in the mouth of the patient. The first magnetic material may be disposed in a first carrier member removably positioned against the flexible member and the second magnetic material may be disposed in the carrier member which comprises a second carrier member which is structured to be removeably disposed in the mouth of the patient.

The flexible member may be a portion of a nasal pillow, the second magnetic material may be positioned in or on the carrier member, and the carrier member may be structured to be positioned across the nose of the patient.

The nasal pillow may comprise a third magnetic material positioned therein or thereon which is positioned and structured to interact with a magnetic material of another nasal pillow in an attractive manner when the nasal pillow is engaged with a nare of the patient.

The third magnetic material may be positioned and structured to interact with the first magnetic material in a repulsive manner. The flexible member may be a portion of a nasal pillow, the second magnetic material may be positioned in or on a portion of the patient interface device, and the portion of the patient interface device may comprise another nasal pillow.

The flexible member may be a portion of a nasal pillow, the second magnetic material may be positioned in or on the carrier member which comprises a second carrier member, the second carrier member may be structured to be positioned across the nose of the patient, and the first magnetic material may be positioned on or in a first carrier member which is disposed on an inner surface of the flexible member.

Another object of the present invention is to provide a cushion for use in a patient interface device for delivering a flow of breathing gas to an airway of a patient. The cushion includes a sealing arrangement as previously described. A further object of the present invention is to provide a patient interface device for delivering a flow of breathing gas to an airway of a patient. The patient interface device includes a cushion having a sealing arrangement as previously described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the word "patient" or "user" shall be used interchangeably to refer to the person to which the interface device is delivering a flow of breathing gas. As used herein, the phrase "removably positioned" shall be used to refer to an element which may be placed on a surface of, in an orifice (i.e., mouth, nostril), or about a user, and subsequently removed therefrom, without the use of any tools. In contrast, an element which is disposed within tissue, e.g., via surgically implantation, is not "removably positioned" as used herein.

As used herein, the phrase "on user" shall mean an element is disposed generally against an external surface of a user. As used herein, the phrase "in a user" shall mean an element is disposed within an orifice (i.e., mouth, nostril(s)) of a user. An element which is implanted within tissue (i.e., not just placed on the surface of tissue) such as via surgical or other means is not considered to be "in a user" as such phrase is used herein. As used herein, the phrase "sealingly engage" shall mean elements which contact each other in a manner such that a generally air-tight seal is formed therebetween.

As used herein in arrangements in which attractive forces are utilized, a "first magnetic material" and a "second magnetic material" include a material that is attracted to iron or steel, e.g., a typical magnet, and a material such as iron, steel, or another magnet to which the first material is attracted. It is understood that the purpose of the "first magnetic material" and the "second magnetic material" in such arrangements is to have the two materials magnetically attracted to each other. Thus, two non-magnetized materials, e.g. two pieces of normal steel, are not a "first magnetic material" and a "second magnetic material" in such arrangements.

As used herein in arrangements in which repulsive forces are utilized, a "first magnetic material" and a "second magnetic material" include a material that is attracted to iron or steel, e.g., a typical magnet, and a second material that is repelled from the first material, e.g., a second magnet arranged with a common pole facing the first magnet. It is understood that the purpose of the "first magnetic material" and the "second magnetic material" in such arrangements is to have the two materials magnetically repelled away from each other. Thus, a magnetized material and a non-magnetized materials, e.g. a magnet and a piece of normal steel, are not a "first magnetic material" and a "second magnetic material" in such arrangements.

As used herein, two or more elements which interact in an "attractive manner" are generally drawn toward each other via magnetic forces (e.g., without limitation, two magnets which are arranged having opposing poles (i.e., N-S, S-N) facing each other).

As used herein, two or more elements which interact in a "repulsive manner" are generally repelled away from each other via magnetic forces (e.g., without limitation, two magnets which are arranged having the same poles (i.e., N-N, S-S) facing each other).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
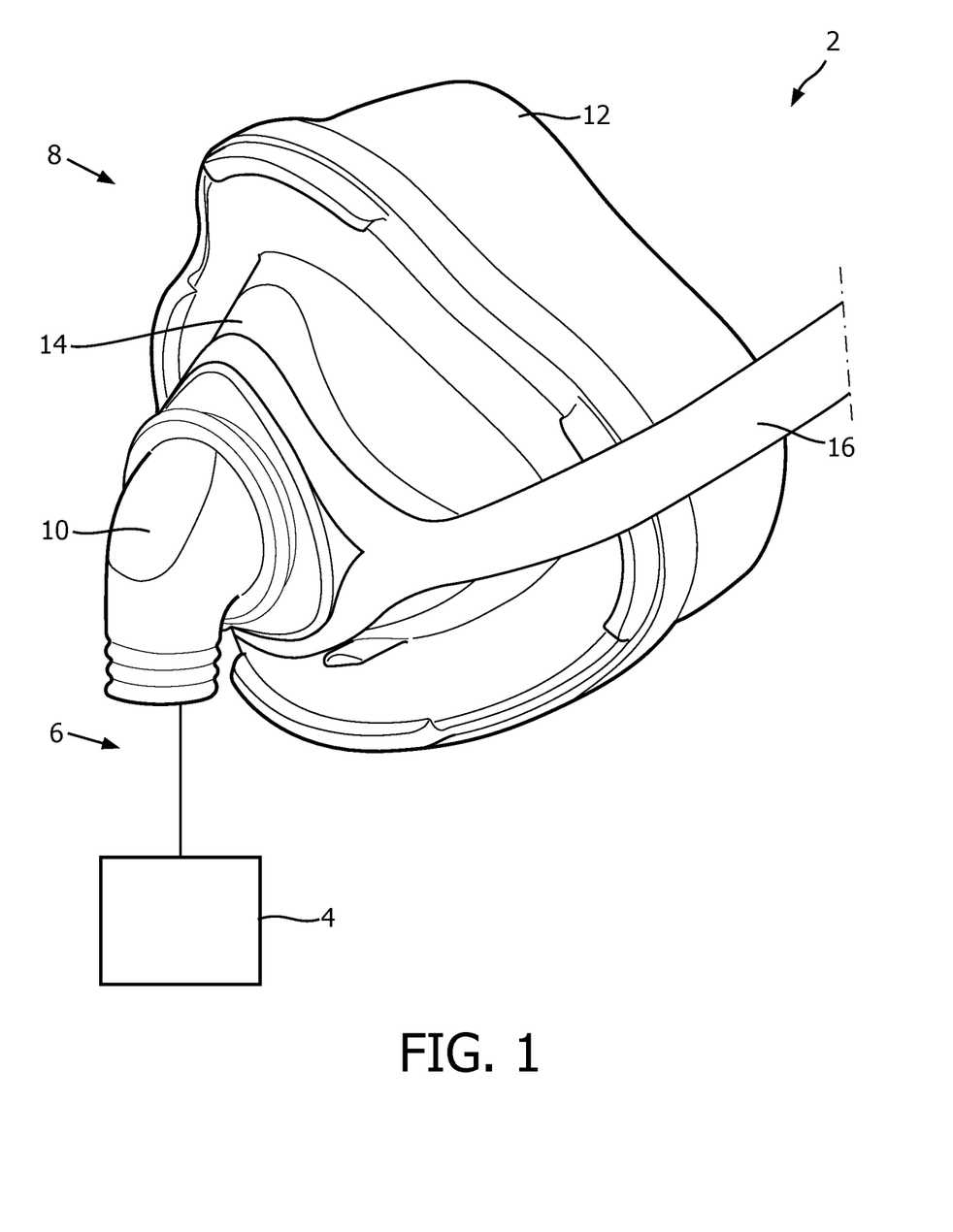
FIG. 1 is a front isometric view of a patient interface device and a portion of a conduit shown connected to a gas flow/pressure generating system (shown schematically) to form a system adapted to provide a regiment of respiratory therapy to a patient according to one exemplary embodiment of the invention.

A system 2 adapted to provide a regimen of respiratory therapy to a patient according to one exemplary embodiment of the invention is generally shown in FIG. 1. System 2 includes a pressure generating device 4 (shown schematically), a delivery conduit 6 (shown partially schematically), and a patient interface device 8 having a fluid coupling conduit 10 coupled thereto. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and user interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

In the exemplary embodiment illustrated in FIG. 1, patient interface device 8 is depicted as a nasal mask which includes a user sealing assembly or cushion 12 coupled to a generally rigid frame 14 which is coupled to conduit 6 via fluid coupling conduit 10. However, it is to be appreciated that other types of patient interface devices, such as, without limitation, a nasal pillows mask, an oral mask, a nasal/oral mask, or a full/total face mask (which encompasses the entire face), which facilitates the delivery of the flow of breathing gas to the airway of a user, may be substituted for patient interface device 8 while remaining within the scope of the present invention. It is also to be appreciated that conduit 6 may be directly coupled to patient interface device 8 without the use of any intermediary coupling, such as conduit 10. Patient interface device 8 may be secured to the head of a patient via a suitable headgear 16, which is also shown for exemplary purposes only.

Figure 2:
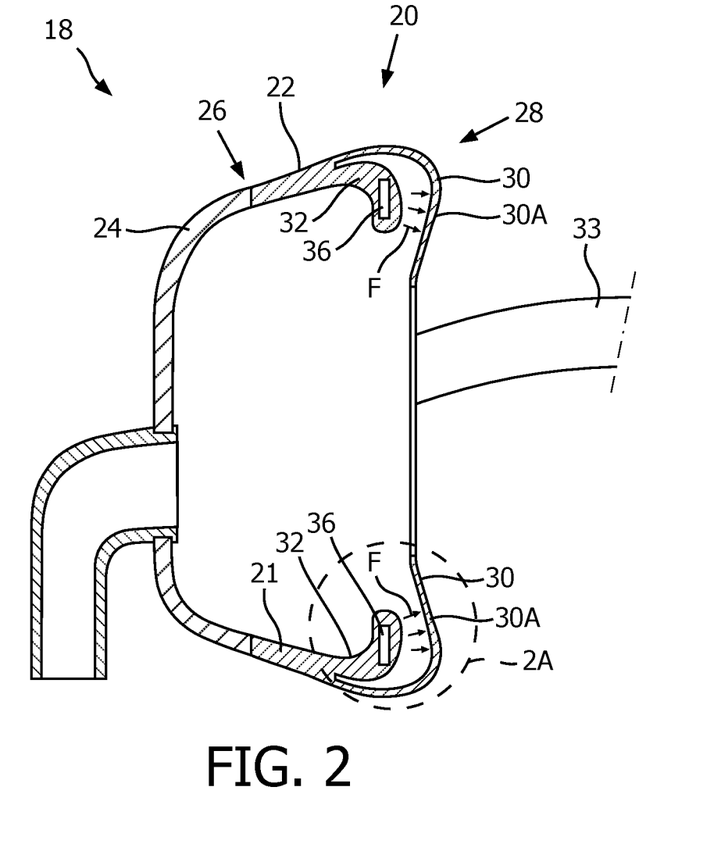
FIG. 2 is a partially schematic sectional view of a patient interface device according to an exemplary embodiment of the invention.

Referring now to FIG. 2, a partially schematic sectional view of an example embodiment of a patient interface device 18 including a sealing arrangement 20 in accordance with the present invention is shown. Similar to patient interface device 8, patient interface device 18 includes a user sealing assembly or cushion 22 which is coupled to a generally rigid frame 24. Cushion 22 is generally formed from a conformable material (e.g., without limitation, silicone, TPE (ThermoPlastic Elastomer), vinyl, elastomeric material, foam, fabric, latex rubber). Cushion 22 includes a first end 26 coupled to frame 24 and an opposite second end 28 which includes sealing arrangement 20 which is structured to sealingly engage a surface of a patient (not shown)

at or about an airway of the patient. More particularly, sealing arrangement 20 includes a flexible member in the form of a sealing flap 30 having a sealing surface 30A which, in the example shown in FIG. 2, is structured to sealingly engage a patient's face about the mouth of a patient. Although FIG. 2 shows an example of an oral mask (i.e., one that only covers the mouth of a patient), it is to be appreciated, however, that the general concept described herein with regard to the arrangement shown in FIG. 2 may also be readily applied to other interface arrangements (i.e., nasal masks, oral/nasal masks, full/total face masks).

Continuing to refer to FIG. 2, sealing arrangement 20 further includes one or more support portions 32 which are positioned to generally underlie sealing flap 30 and structured to physically urge sealing flap 30 toward the face of a user when frame 24 is urged toward the face of a user via a headgear strap 33 or other suitable arrangement. Sealing flap 30 and support portions 32 are integrally formed portions of cushion 22 which, as previously discussed, is formed from a conformable material. However, as shown partially schematically in FIG. 2A, sealing flap 30 further includes a first magnetic material 34 (shown schematically) which is positioned therein or thereon in a predetermined manner to interact with a second magnetic material 36 (shown schematically), which is positioned in or on support portion 32. More particularly, first magnetic material 34 and second magnetic material 36 have their respective magnetic poles oriented such that first magnetic material 34 is repelled by second magnetic material 36. As frame 24, and thus support portion 32 and second magnetic material 36, are urged toward the face of the patient via strap 33, sealing flap 30 (and sealing surface 30A thereof) is also further urged toward the face of the patient by the repulsive magnetic force(s) F resulting from the interaction of the magnetic fields produced by first magnetic material 34 and second magnetic material 36.

Figure 2A:
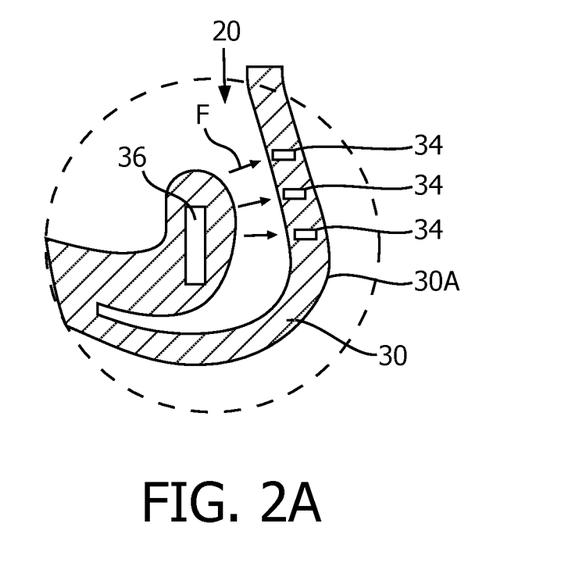
FIG. 2A is a detailed view of the portion of the patient interface device indicated at 2A in FIG. 2.

First magnetic material 34 may be arranged as a plurality of small magnetic particles dispersed within, or as a coating provided on, sealing flap 30. For example, the material may be added as a magnetic powder from pulverized magnets. The powder may be added to uncured silicone and injection molded in sealing flap 30. To orient the poles of the magnetic particles in the desired orientation, the tool could include magnets inserted in the orientation that would attract a certain pole of each magnet. As the material surrounding the magnetic particles cures, the magnetic particles are effectively locked in position. As another example, magnetic material 34 could be in the form of a thin magnetic material that was already magnetized then reformed to create sealing flap 30. As yet another example, iron particles can be incorporated into the cushion via compounding and then formed into a sealing flap. After formation, the material in the flap can be magnetized similarly to the way magnets are created today through an induced electrical magnetic field. First magnetic material 34 may also take the form of one or more discrete preformed magnets (e.g., without limitation, cylindrical magnets) which are disposed within, or provided on, sealing flap 30 (e.g., without limitation, such magnets could be overmolded or glued in place with the assistance of a suitable jig.

Similarly, second magnetic material 36 may be arranged as a plurality of small magnetic particles dispersed within, or as a coating provided on, support portion 32. Alternatively, second magnetic material 36 may take the form of one or more discrete preformed magnets which are disposed within, or provided on, support portion 32. Although shown as being placed in locations which would lie generally above and below the mouth of a patient, it is to be appreciated that such magnetically interacting portions (i.e., first magnetic material 34 and second magnetic material 36) may be located in sealing arrangement 20 generally anywhere along the opening of the patient's mouth as desired to provide an improved seal in such areas.

In another example embodiments in accordance with the present invention, one or both of first magnetic material 34 and/or second magnetic material 36 may be provided as a part of a kit which includes other materials (e.g., without limitations, a suitable adhesive) for custom placing one or both of magnetic materials 34 and/or 36 on a cushion as a sort of retrofit application.

Figure 3:
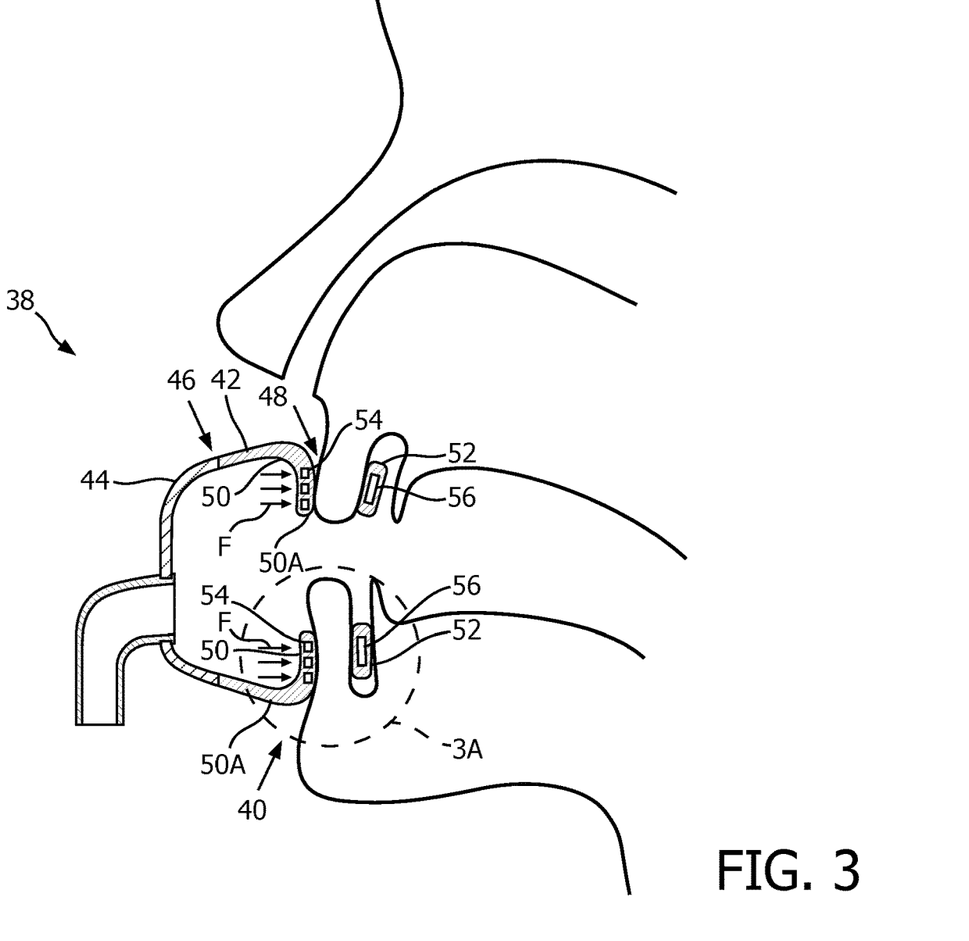
FIG. 3 is a partially schematic sectional view of a patient interface device according to another exemplary embodiment of the invention shown disposed on the face of a patient.
Figure 3A:
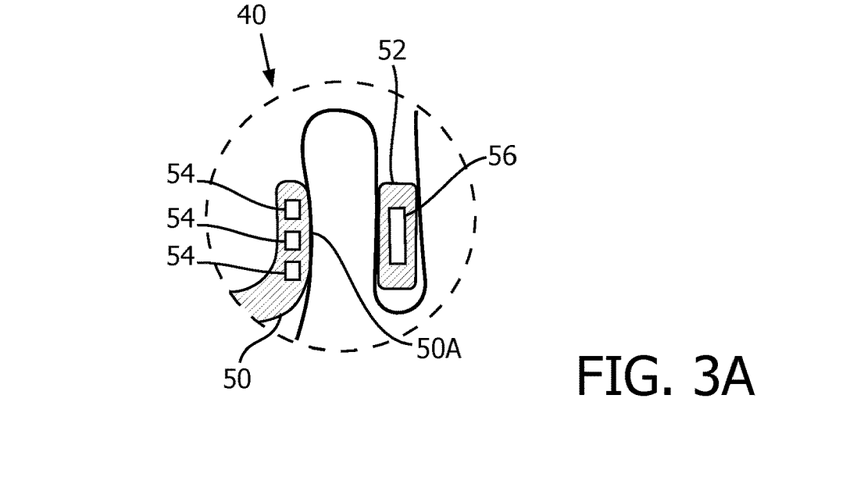
FIG. 3A is a detailed view of the portion of the patient interface device of FIG. 3 indicated at 3A in FIG. 3.

Referring now to FIGS. 3 and 3A, a partially schematic sectional view of another example embodiment of a patient interface device 38 including a sealing arrangement 40 in accordance with the present invention is shown disposed in contact with the face of a patient. Patient interface device 38 includes a user sealing assembly or cushion 42 which is coupled to a generally rigid frame 44. Cushion 42 is generally formed from a conformable material (e.g., without limitation, silicone, TPE, vinyl, elastomeric material, foam, fabric, latex rubber). Cushion 42 includes a first end 46 coupled to frame 44 and an opposite second end 48 (which includes part of sealing arrangement 40) which is structured to sealingly engage a surface of a patient (shown schematic in section, not numbered) at or about an airway of the patient.

More particularly, sealing arrangement 40 includes a sealing flap 50 having a sealing surface 50A which, in the example shown in FIG. 3, is structured to sealingly engage a patient's face about the mouth of a patient. Sealing flap 50 is integrally formed as a portion of cushion 42 and as such is also formed from a conformable material. However, as shown partially schematically in FIG. 3A, sealing flap 50 further includes a first magnetic material 54 which is positioned therein or thereon in a predetermined manner to magnetically interact in an attractive manner with a second magnetic material 56, which is positioned in or on a carrier member 52 that is removably positioned in the mouth of the patient (i.e., in the patient) generally between the lip and gums/teeth of the patient, generally opposite first magnetic material 54.

Figure 3B:
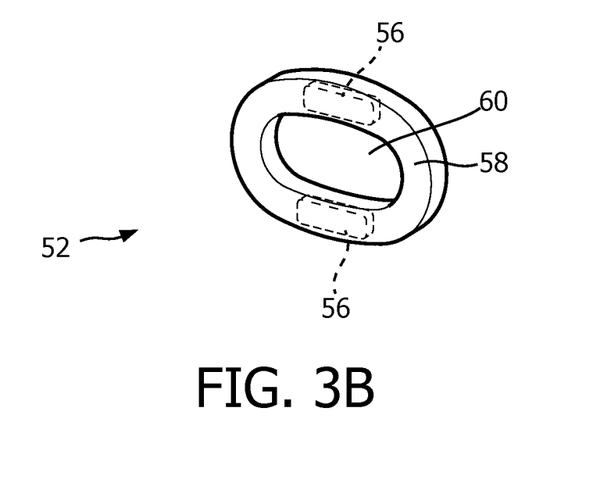
FIGS. 3B-3D are isometric views of example embodiments of carrier members according to the present invention which may be employed in the patient interface device of FIG. 3.
Figure 3C:
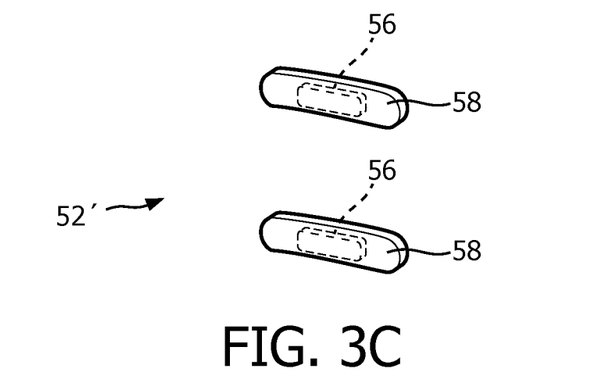
Figure 3D:
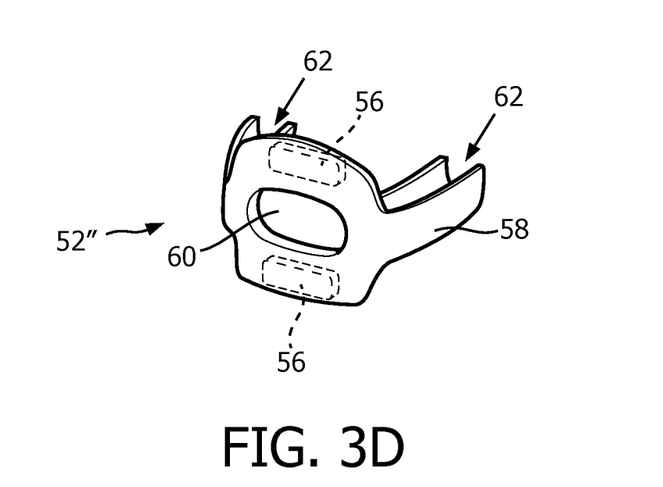

FIGS. 3B-3D show some example embodiments of carrier members 52, 52', 52" which may be used in sealing arrangement 40 of FIG. 3. For example, FIG. 3B shows a carrier member 52 formed from a first material 58 (e.g., without limitation, silicone, TPE, vinyl, elastomeric material, foam, fabric, latex rubber, plastic) having second magnetic material 56 disposed both in upper and lower portions thereof. Carrier member 52 includes a breathing passage 60 formed therethrough which is of sufficient size to generally not obstruct the passage of breathing gas to the airway of the patient. Carrier member 52' of FIG. 3C is of generally similar construction as carrier member 52 except carrier member 52' does not include any portions connecting the upper and lower portions thereof.

Carrier member 52" of FIG. 3D is formed in a similar shape as an athletic mouthpiece or mouthguard and as such includes upper and lower channels (only upper channel 62 is visible in FIG. E) which are each structured to be engaged by either the upper or lower teeth of a user. Similar to carrier member 52 of FIG. 3, carrier member 52" also includes a breathing passage 60 formed therethrough which is of sufficient size to not obstruct the passage of breathing gas to the airway of the patient. It is to be appreciated that each of such carrier members 52, 52', 52" are arranged so as to position second magnetic material 56 in a manner such that first magnetic material 54 of sealing flap 50 is attracted thereto, and thus sealing flap 50 and sealing surface 50A thereof is urged toward the face of the patient (such as shown by arrows F in FIG. 3).

First magnetic material 54 may be arranged as a plurality of small magnetic particles dispersed within, or provided on, sealing flap 50 (e.g., such as described elsewhere herein). Alternatively, first magnetic material 54 may take the form of one or more discrete preformed magnets (e.g., such as described elsewhere herein) which are disposed within, or provided on, sealing flap 50. Similarly, second magnetic material 56 may be arranged as a plurality of small magnetic particles dispersed within, or as a coating provided on, carrier member 52 (such as described elsewhere herein). Alternatively, second magnetic material 56 may take the form of one or more discrete preformed magnets which are disposed within, or provided on, carrier member 52 (e.g., such as described elsewhere herein). Although shown as being placed in locations which would lie generally above and below the mouth of a patient, it is to be appreciated that such magnetically interacting portions (i.e., first magnetic material 54 and second magnetic material 56) may be located in sealing arrangement 40 generally anywhere along the opening of the patient's mouth as desired to provide an improved seal in such areas.

Although FIG. 3 shows an example of an oral mask (i.e., one that only covers the mouth of a patient), it is to be appreciated, however, that the general concept described herein with regard to the arrangement shown in FIG. 3 may also be readily applied to other interface arrangements (i.e., nasal masks, oral/nasal masks, full/total face masks). It is also to be appreciated that the arrangement shown in FIG. 3 may be used in conjunction with a suitable headgear arrangement or, in applications where sufficient magnetic forces are created between first magnetic material 54 an second magnetic material 56, without a headgear arrangement.

Figure 4:
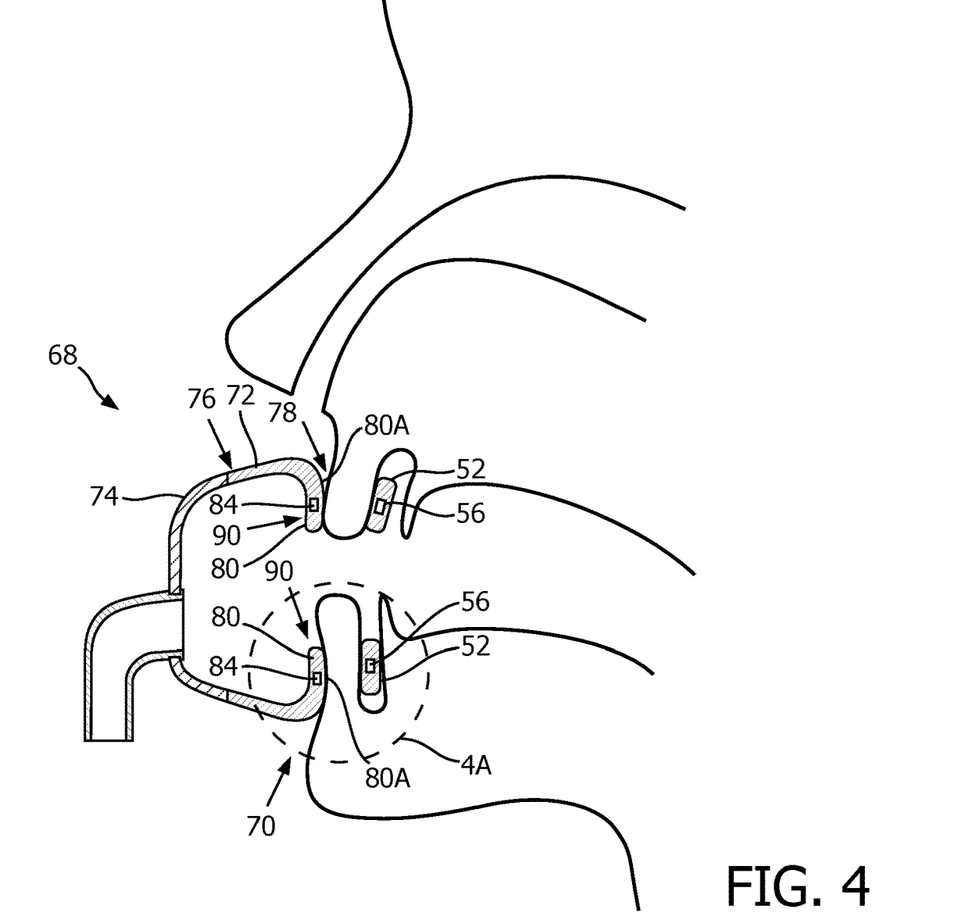
FIG. 4 is a partially schematic sectional view of yet another patient interface device according to an exemplary embodiment of the invention shown disposed on the face of a patient.
Figure 4A:
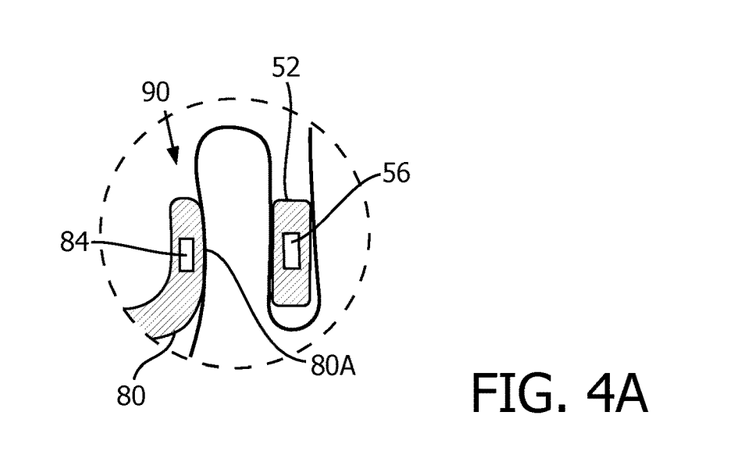
FIG. 4A is a detailed view of the portion of the patient interface device of FIG. 4 indicated at 4A in FIG. 4.

Referring now to FIGS. 4 and 4A, a partially schematic sectional view of yet another example embodiment of a patient interface device 68 including a sealing arrangement 70 in accordance with the present invention disposed in contact with the face of a patient is shown. Patient interface device 68 includes a user sealing assembly or cushion 72 which is coupled to a generally rigid frame 74. Cushion 72 is generally formed from a conformable material (e.g., without limitation, silicone, TPE, vinyl, elastomeric material, foam, fabric, latex rubber). Cushion 72 includes a first end 76 coupled to frame 74 and an opposite second end 78 (which includes part of sealing arrangement 70) which is structured to sealingly engage a surface of a patient (shown schematic in section, not numbered) at or about an airway of the patient. More particularly, sealing arrangement 70 includes a sealing flap 80 having a sealing surface 80A which, in the example shown in FIG. 4, is structured to sealingly engage a patient's face about the mouth of a patient. Sealing flap 80 is integrally formed as a portion of cushion 72 and as such is also formed from conformable first material 71.

Figure 4B:
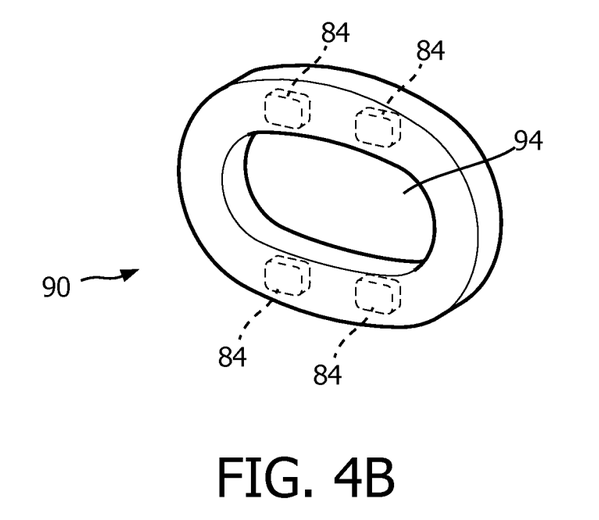
FIGS. 4B-4C are isometric views of example embodiments of carrier members according to the present invention which may be employed in the patient interface device of FIG. 4.
Figure 4C:
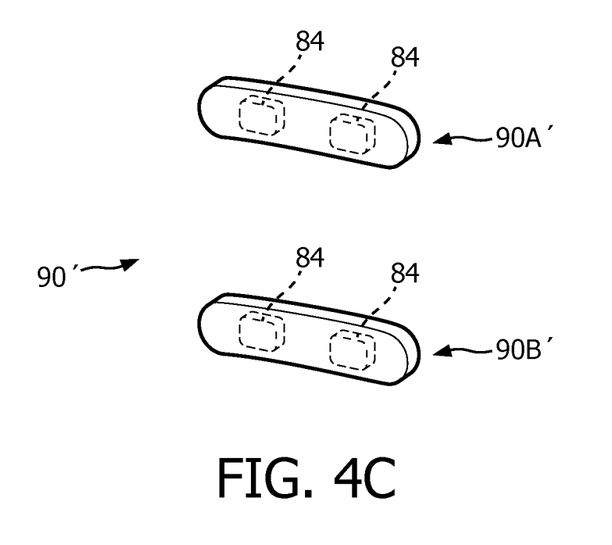

Continuing to refer to FIGS. 4 and 4A, as well as to FIG. 4B, sealing arrangement 70 further includes a first carrier member 90 removably positioned within cushion 72 against (i.e., on) an inner surface (not numbered) of sealing flap 80 opposite sealing surface 80A. First carrier member 90 includes a breathing passage 94 formed therethrough which is of sufficient size to not obstruct the passage of breathing gas to the airway of the patient. First carrier member 90 is formed from a conformable material (e.g., such as described elsewhere herein) having a first magnetic material 84 disposed both in or on upper and lower portions thereof. In another example embodiment, such as illustrated in FIG. 4C, an alternative first carrier member 90' may be formed from two sub-portions 90A', 90B', each having first magnetic material 84 disposed therein or thereon. First magnetic material 84 is positioned in or on first carrier member 90 in a predetermined position to magnetically interact in an attractive manner with a second magnetic material, such as second magnetic material 56, which is positioned in a second carrier member, such as any of the example carrier members 52, 52', 52" previously described in conjunction with FIGS. 3B-3D, that is removably positioned in the mouth of the patient (i.e., in the patient generally between the lip and gums/teeth) generally opposite first magnetic material 84.

First magnetic material 84 may be arranged as a plurality of small magnetic particles dispersed within, or provided on, first carrier member 90. Alternatively, first magnetic material 84 may take the form of one or more discrete preformed magnets (e.g., such as described elsewhere herein) which are disposed within, or provided on, first carrier member 90. Second magnetic material 56 may be arranged relative to carrier member 52 in any of the manners previously discussed. Although shown as being placed in locations which would lie generally above and below the mouth of a patient, it is to be appreciated that such magnetically interacting portions (i.e., first magnetic material 84 and second magnetic material 56) may be located in sealing arrangement 70 generally anywhere along the opening of the patient's mouth as desired to provide an improved seal in such areas.

Although FIG. 4 shows an example of an oral mask (i.e., one that only covers the mouth of a patient), it is to be appreciated, however, that the general concept described herein with regard to the arrangement shown in FIG. 4 may also be readily applied to other interface arrangements. It is also to be appreciated that the arrangement shown in FIG. 4 may be used in conjunction with a suitable headgear arrangement or, in applications where sufficient magnetic forces are created between first magnetic material 84 an second magnetic material 56, without a headgear arrangement.

Figure 5:
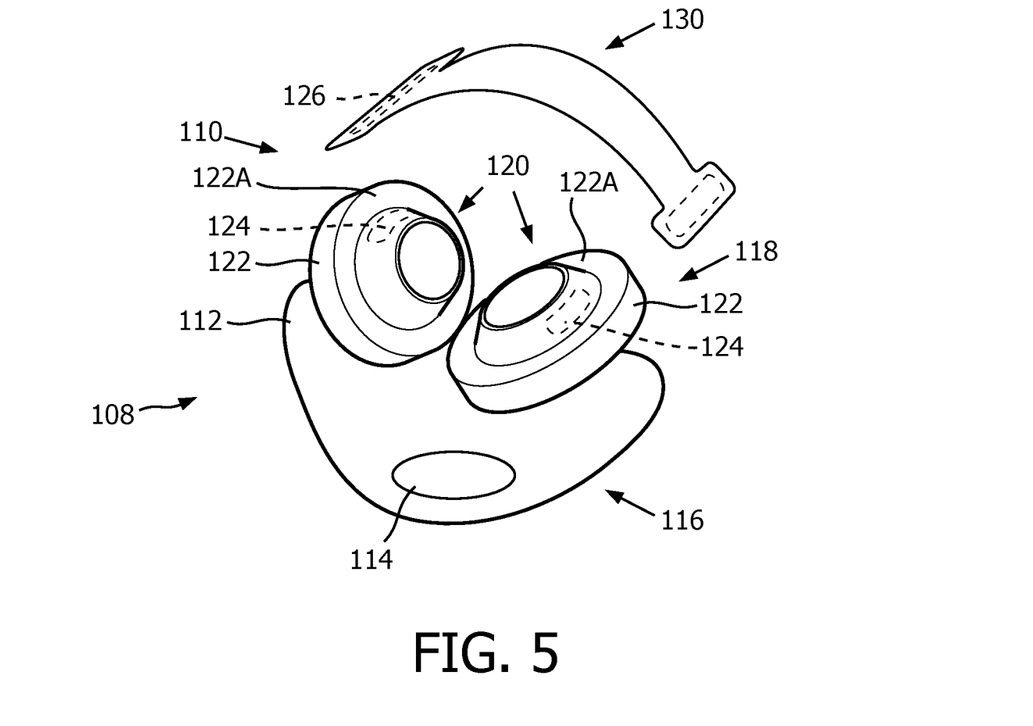
FIG. 5 is a partially schematic isometric view of yet another patient interface device according to an exemplary embodiment of the invention.
Figure 5A:
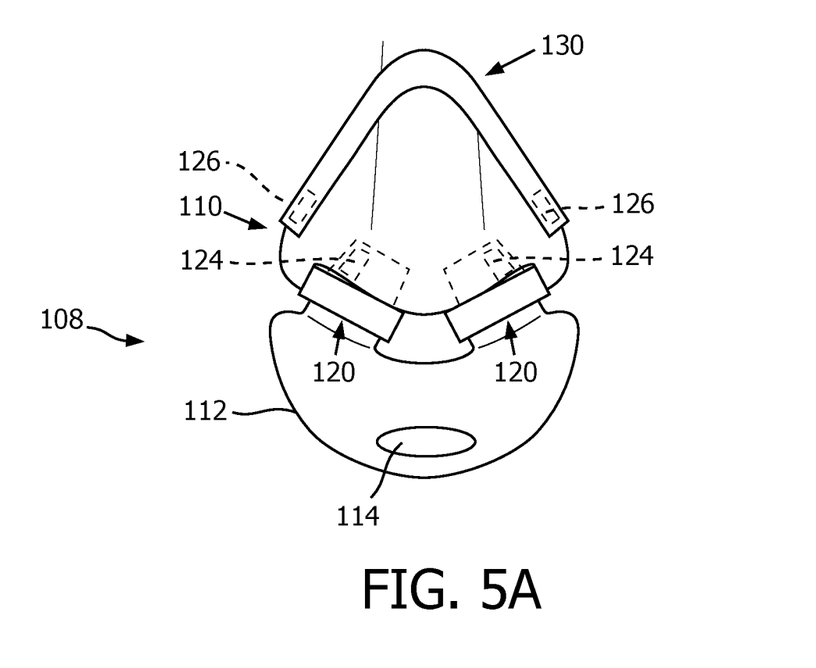
FIG. 5A is a front elevation view of the patient interface device of FIG. 5 shown disposed on the face of a patient.

Referring now to FIGS. 5 and 5A, a partially schematic isometric view of another example embodiment of a patient interface device 108 in the form of a nasal pillows mask having a sealing arrangement 110 in accordance with the present invention is shown by itself (FIG. 5) and disposed in contact with the face of a patient (FIG. 5A). Patient interface device 108 includes a user sealing assembly or cushion 112 having a supply aperture 114 which is adapted to be coupled to a conduit or other suitable member for providing a supply of treatment gas therein. Cushion 112 is generally formed from a conformable material (e.g., without limitation, silicone, TPE, vinyl, elastomeric material, foam, fabric, latex rubber). Cushion 112 generally includes a first end 116 having supply aperture 114 disposed therein or about, and an opposite second end 118 having a pair of nasal pillows 120 which are each structured to sealingly engage a surface of a patient (shown schematically, not numbered) at or about an airway of the patient. More particularly, each nasal pillow 120 includes a sealing flap 122 having a sealing surface 122A which is structured to sealingly engage a patient's face/nose about a nostril of a patient. Sealing flap 122 is formed from a conformable material (e.g., such as described elsewhere herein) and may be formed separately from, or integrally with, cushion 112.

Figure 5B:
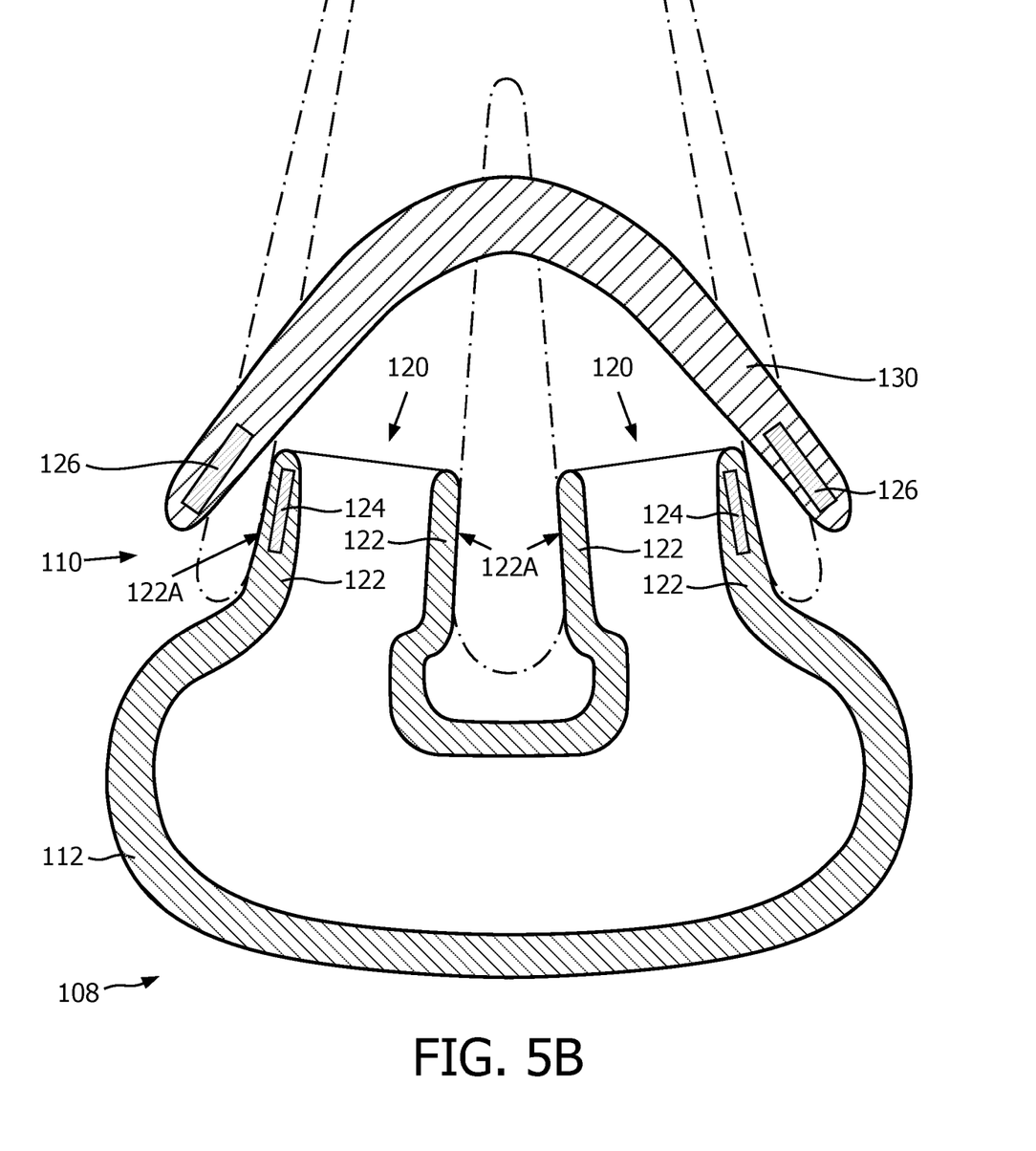
FIG. 5B is a sectional view of the arrangement of FIG. 5A viewed in a plane generally parallel to the facial plane of the patient showing details of the engagement between portions of the patient interface and corresponding surfaces of the nasal structure of the patient.

Continuing to refer to FIGS. 5 and 5A, as well as to FIG. 5B (which shows a sectional view of the arrangement of FIG. 5A in a plane generally parallel to the facial plane of the patient), sealing flap 122 further includes a first magnetic material 124 (shown schematically) which is positioned therein in a predetermined manner to magnetically interact in an attractive manner with a second magnetic material 126 (shown schematically), which is positioned in a carrier member 130 that is removably positioned on the nose of the patient generally spanning across the nose and disposed slightly upward from the nostrils of the patient. Carrier member 130 is positioned such that second magnetic material 126 is thus disposed generally opposite first magnetic material 124 such that second magnetic material 126 and first magnetic material 124 magnetically interact in an attractive manner. Such attractive magnetic interaction acts to urge sealing surface 122A of sealing flap 122 toward the surface of the patient, thus improving the seal between sealing flap 122 and generally the alar rim of the patient's nose.

First magnetic material 124 may be arranged as a plurality of small magnetic particles dispersed within, or provided on, sealing flap 122. Alternatively, first magnetic material 124 may take the form of one or more discrete preformed magnets (e.g., such as described elsewhere herein) which are disposed within, or provided on, sealing flap 122. Second magnetic material 126 may be arranged relative to carrier member 130 in any of the manners previously discussed.

Figure 6:
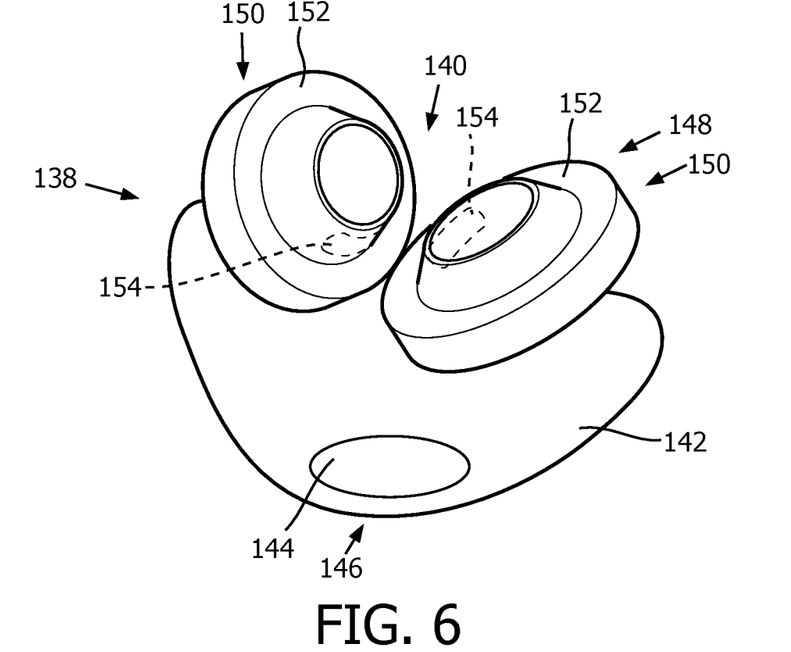
FIG. 6 is a partially schematic isometric view of yet another patient interface device according to an exemplary embodiment of the invention.
Figure 6A:
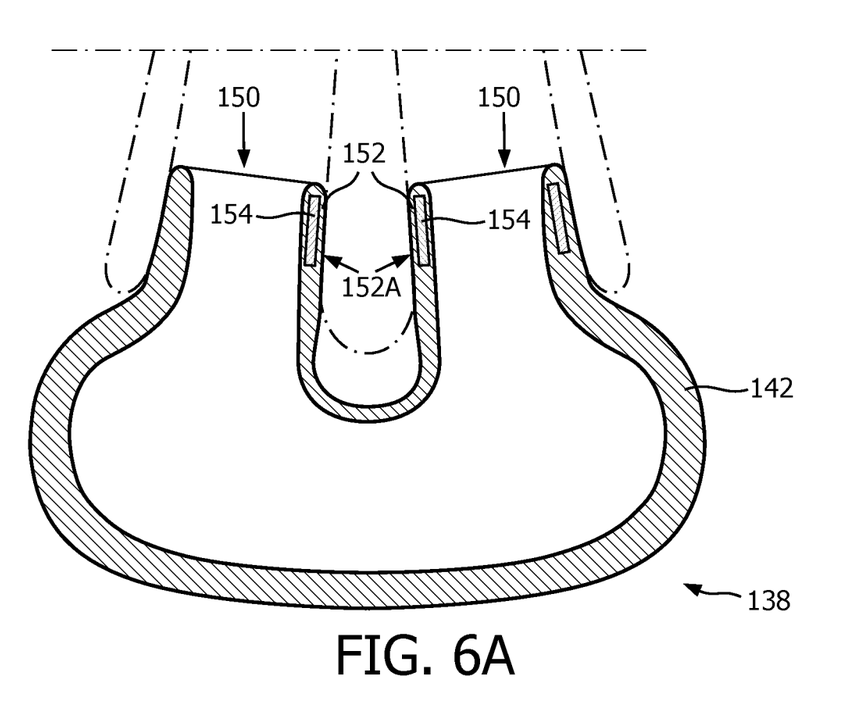
FIG. 6A is a sectional view of the arrangement of FIG. 6 disposed in contact with the nostrils of a patient, viewed in a plane disposed generally parallel to the facial plane of the patient showing details of the engagement between portions of the patient interface and corresponding surfaces of the nasal structure of the patient.

Referring now to FIGS. 6 and 6A, a partially schematic isometric view of another example embodiment of a patient interface device 138 in the form of a nasal pillows mask having a sealing arrangement 140 in accordance with the present invention is shown by itself (FIG. 6) and in a section view (FIG. 6A) showing device 138 disposed in contact with the nose of a patient in a plane parallel to a facial plane of the patient. Patient interface device 138 includes a user sealing assembly or cushion 142 having a supply aperture 144 which is adapted to be coupled to a conduit or other suitable member for providing a supply of treatment gas therein. Cushion 142 is generally formed from a conformable material (e.g., without limitation, silicone, TPE, vinyl, elastomeric material, foam, fabric, latex rubber). Cushion 142 generally includes a first end 146 having supply aperture 134 disposed therein or about, and an opposite second end 148 having a pair of nasal pillows 150 which are each structured to sealingly engage a surface of a patient (shown schematically in partial dashed line, not numbered) at or about an airway of the patient. More particularly, each nasal pillow 150 includes a sealing flap 152 having a sealing surface 152A which is structured to sealingly engage a patient's face/nose about a nostril of a patient. Each sealing flap 152 is formed from a conformable material the same as, or similar to, cushion 142 and may be formed separately from, or integrally with, cushion 142.

Continuing to refer to FIGS. 6 and 6A, each sealing flap 152 further includes a magnetic material 154 (shown schematically) which is positioned therein in a predetermined manner to magnetically interact in an attractive manner with the magnetic material 152 of the other sealing flap 152. Hence, in the example shown in FIG. 6A, such magnetic attraction between the magnetic material 154 of each sealing flap 152 urges sealing surfaces 152A toward each other, thus improving the seal between each sealing flap 152 and the nasal septum of the patient.

Magnetic material 154 may be arranged as a plurality of small magnetic particles dispersed within, or provided on, sealing flap 152. Alternatively, magnetic material 154 may take the form of one or more discrete preformed magnets (e.g., such as described elsewhere herein) which are disposed within, or provided on, sealing flap 152.

Figure 7:
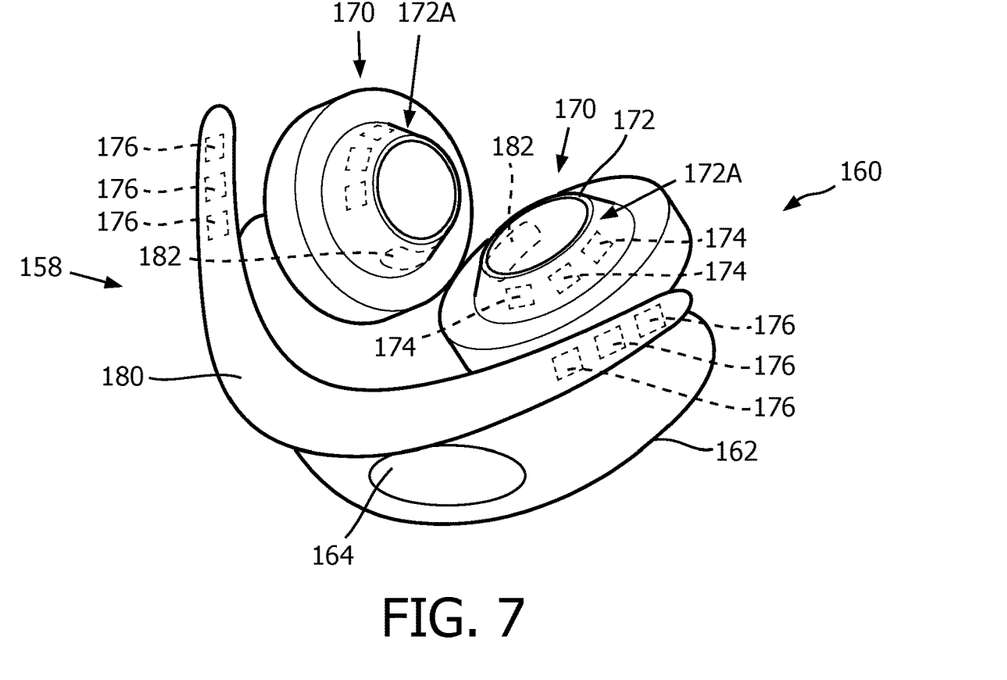
FIG. 7 is a partially schematic isometric view of yet another patient interface device according to an exemplary embodiment of the invention.
Figure 7A:
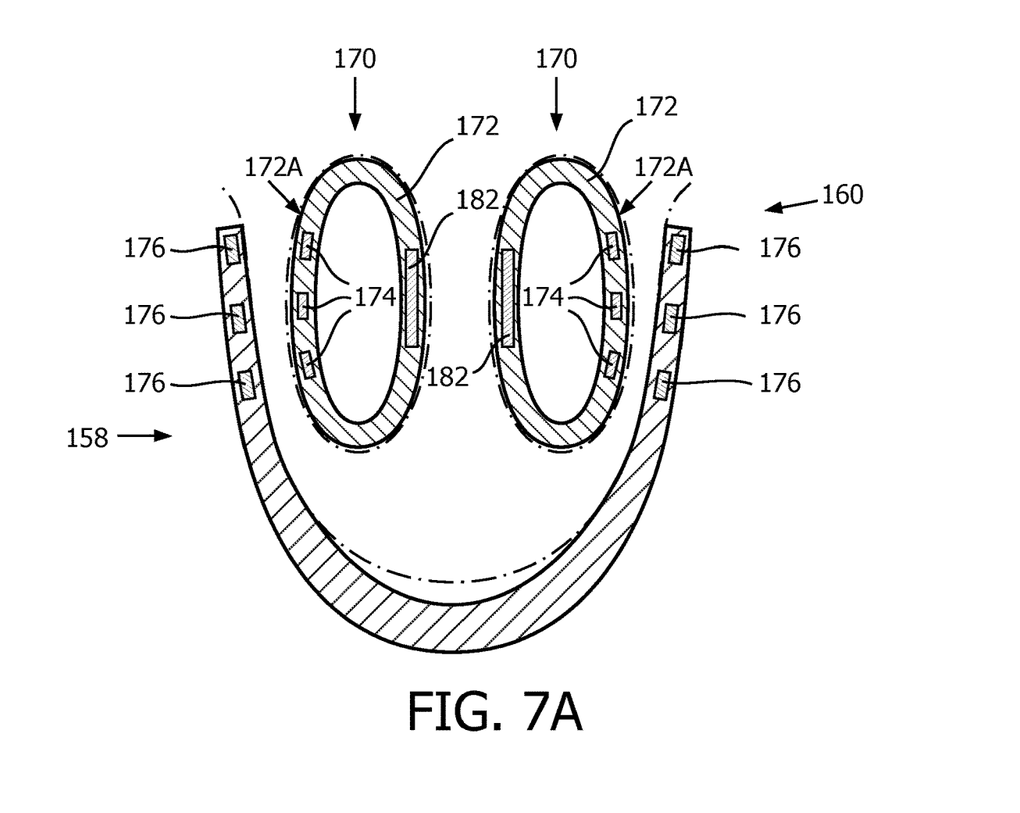
FIG. 7A is a sectional view of the arrangement of FIG. 7 disposed in contact with the nostrils of a patient, viewed in a plane generally perpendicular to the facial plane of the patient showing details of the engagement between portions of the patient interface and corresponding surfaces of the nasal structure of the patient.

Referring now to FIGS. 7 and 7A, a partially schematic isometric view of another example embodiment of a patient interface device 158 in the form of a nasal pillows mask having a sealing arrangement 160 in accordance with the present invention is shown by itself (FIG. 7) and in a section view (FIG. 7A) showing device 158 disposed in contact with the nose of a patient in a plane perpendicular to a facial plane of the patient. Patient interface device 158 includes a user sealing assembly or cushion 162 having a supply aperture 164 which is adapted to be coupled to a conduit or other suitable member for providing a supply of treatment gas therein. Cushion 162 is generally formed from a conformable material (e.g., without limitation, silicone, TPE, vinyl, elastomeric material, foam, fabric, latex rubber). Cushion 162 includes a pair of nasal pillows 170 which are each structured to sealingly engage a surface of a patient (shown schematically in partial dashed line, not numbered) at or about an airway of the patient. More particularly, each nasal pillow 170 includes a sealing flap 172 having a sealing surface 172A which is structured to sealingly engage a patient's face/nose about a nostril of a patient. Sealing flap 172 is formed from a conformable material the same as, or generally similar to cushion 162 and may be formed separately from, or integrally with, cushion 162.

Sealing flap 172 includes a first magnetic material 174 (shown schematically) which is positioned therein in a predetermined manner to magnetically interact in an attractive manner with a second magnetic material 176 (shown schematically), which is positioned in a carrier member 180 that is removably positioned on the nose of the patient generally spanning across the nose and disposed slightly upward from the nostrils of the patient. Carrier member 180 is positioned such that second magnetic material 176 is thus disposed generally opposite first magnetic material 174 such that second magnetic material 176 and first magnetic material 174 magnetically interact in an attractive manner. Such attractive magnetic interaction acts to urge sealing surface 172A of sealing flap 172 toward the surface of the patient, thus improving the seal between sealing flap 172 and generally the alar rim of the patient's nose.

Continuing to refer to FIGS. 7 and 7A, each sealing flap 172 further includes a third magnetic material 182 (shown schematically) which is positioned therein in a predetermined manner to magnetically interact in an attractive manner with the magnetic material 182 of the other sealing flap 172 as well as to magnetically interact in a repulsive manner with the magnetic material 174 of the same sealing flap 172. Hence, in the example shown in FIG. 7A, the magnetic attraction between magnetic material 182 of each sealing flap 172 urges sealing surfaces 172A of each sealing flap 172 toward each other, thus improving the seal between each sealing flap 172 and the nasal septum of the patient. At the same time, the magnetic repulsion between magnetic material 174 and magnetic material 182 of the same sealing flap 172 helps to keep each nasal pillow 170 open.

Each magnetic material 174 and 182 may be arranged as a plurality of small magnetic particles dispersed within, or provided on, sealing flap 172. Alternatively, magnetic materials 174 and 182 may take the form of one or more discrete preformed magnets (e.g., such as described elsewhere herein) which are disposed within, or provided on, sealing flap 182. Magnetic material 176 may be arranged relative to carrier member 180 in any of the manners previously discussed.

Figure 8:
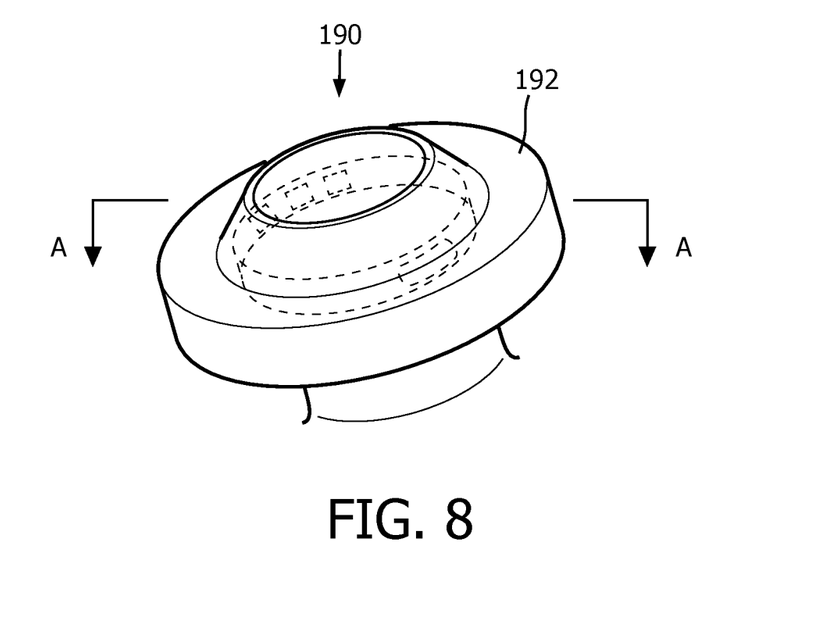
FIG. 8 is an isometric view of a portion of a patient interface device according to an exemplary embodiment of the invention.
Figure 8A:
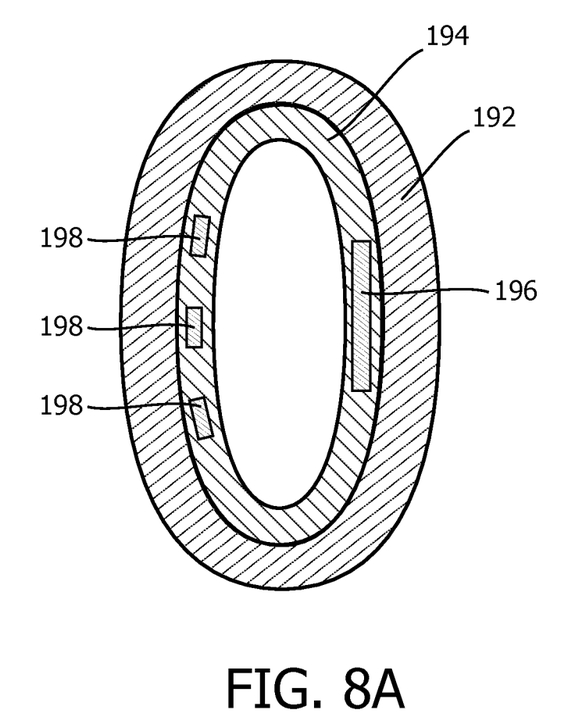
FIG. 8A is a sectional view of the portion of the patient interface device of FIG. 8 taken along line A-A of FIG. 8.

Referring now to FIG. 8, a single pillow 190 of a patient interface device in accordance with an example embodiment of the present invention is shown. Pillow 190 is of similar construction as the pillow members previously described herein and thus includes a sealing flap 192. However, unlike the other pillows members described herein, pillow member 190 does not include any magnetic material disposed therein. Instead, magnetic material 196, 198 is disposed in a carrier member 194 which is disposed on an inner surface of sealing flap 192. Carrier member 194 is formed from a conformable material (e.g., such as described elsewhere herein) which may be readily positioned in, or removed from, pillow 190.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A sealing arrangement for use in a patient interface device for delivering a flow of breathing gas to an airway of a patient, the sealing arrangement comprising:
   (a) a nasal pillow having a sealing surface structured to sealingly engage a surface of the patient at or about the airway;
   (b) a first magnetic material disposed in or on the nasal pillow;
   (c) a carrier member structured to be positioned across a nose of the patient; and
   (d) a second magnetic material positioned in or on the carrier member, wherein the first magnetic material and the second magnetic material are positioned and structured to magnetically interact in a manner that the sealing surface of the nasal pillow toward the surface of the patient, responsive to the nasal pillow being disposed at or about the airway and the second magnetic material is disposed at a corresponding position to interact with the first magnetic material, wherein the nasal pillow comprises a third magnetic material positioned therein or thereon which is positioned and structured to interact with a magnetic material of another nasal pillow in an attractive manner when the nasal pillow engaged with a naris of the patient, and wherein the third magnetic material is positioned and structured to interact with the first magnetic material in a repulsive manner.

2. The sealing arrangement of claim 1, wherein the first magnetic material comprises a plurality of magnetic particles dispersed within, or provided on, the nasal pillow.

3. The sealing arrangement of claim 1, wherein the first magnetic material comprises at least one discrete magnet disposed within, or provided on, the nasal pillow.

* * * * *